US005866375A

United States Patent [19]

Figura et al.

[11] Patent Number: 5,866,375
[45] Date of Patent: Feb. 2, 1999

[54] METHOD FOR THE CULTURE OF MICROORGANISMS OF THE GENERA HELICOBACTER, CAMPYLOBACTER AND ARCOBACTER EMPLOYING CULTURE MEDIA COMPRISING CYCLODEXTRINS

[75] Inventors: Natale Figura; Massimo Bugnoli, both of Monteriggioni; Roberto Olivieri, Costalpino; Rino Rappuoli, Monteriggioni, all of Italy

[73] Assignee: Chiron S.p.A., Italy

[21] Appl. No.: 468,372

[22] Filed: Jun. 6, 1995

Related U.S. Application Data

[63] Continuation-in-part of Ser. No. 295,081, Aug. 24, 1994, which is a continuation of Ser. No. 962,357, Oct. 16, 1992, abandoned.

[30] Foreign Application Priority Data

Oct. 31, 1991 [IT] Italy ................................. MI91A2904

[51] Int. Cl.$^6$ ..................................................... C12P 21/00
[52] U.S. Cl. ...................... 435/71.3; 435/71.1; 435/71.2; 435/822; 530/825
[58] Field of Search ........................... 530/825; 435/71.3, 435/71.2, 71.1, 822

[56] References Cited

U.S. PATENT DOCUMENTS

| 4,500,639 | 2/1985  | Suzuki et al. ............................ 435/244 |
| 4,687,738 | 8/1987  | Ginnaga et al. ........................... 435/68 |
| 4,965,205 | 10/1990 | Millet et al. ........................... 435/252.1 |

FOREIGN PATENT DOCUMENTS

| 0296765   | 12/1988 | European Pat. Off. . |
| WO 93/07273 | 4/1993 | WIPO . |
| WO 93/18150 | 9/1993 | WIPO . |

OTHER PUBLICATIONS

Cover et al, Infect. Immun. 58(3):603–610, 1990.

Buck, G.E. et al., "Medium Supplementation for growht of Campylobacter Pyloridis", *J. of Clin. Microbiol.* 1984, pp. 597–599.

Forman, D. et al., "Association between Infection with *Helicobacter pylori* and Risk of Gastric Cancer: Evidence from a Prospective Investigation", *Brit. Med. J.* 1991, 302, 1302–1305.

Graham, D. and Hazell, "Unsaturated Fatty Acids and Viability of *Helicobacter (Campylobacter) pylori*", *J. of Clin. Microb.* 1990, 28(5), 1060–1061.

Morgan, D. et al., "Growth of *Campylobacter pylori* in Liquid Media", *J. of Clin. Microbiol.* 1987, 25(11), 2123–2125.

Telford, J. et al., "Gene Structure of the *Helicobacter pylori* Cytotoxin and Evidence of Its Key Role in Gastric Disease", *J. Exp. Med.* 1994, 179, 1653–1658.

Thompson, L. et al., "Inhibitory Effect of Polyunsaturated Fatty Acids on the Growth of *Helicobacter pylori*: a Possible Explanation of the Effect of Diet on Peptic Ulceration", *Gut* 1994, 35, 1557–1561.

*Primary Examiner*—Francisco C. Prats
*Attorney, Agent, or Firm*—Woodcock Washburn Kurtz Mackiewicz & Norris, LLP; Alisa A. Harbin; Robert P. Blackburn

[57] ABSTRACT

Method for the culture of microorganisms of the genera Helicobacter, Campylobacter and Arcobacter, wherein culture media are employed, which comprise, in place of blood or its derivative, cyclodextrins.

6 Claims, 4 Drawing Sheets

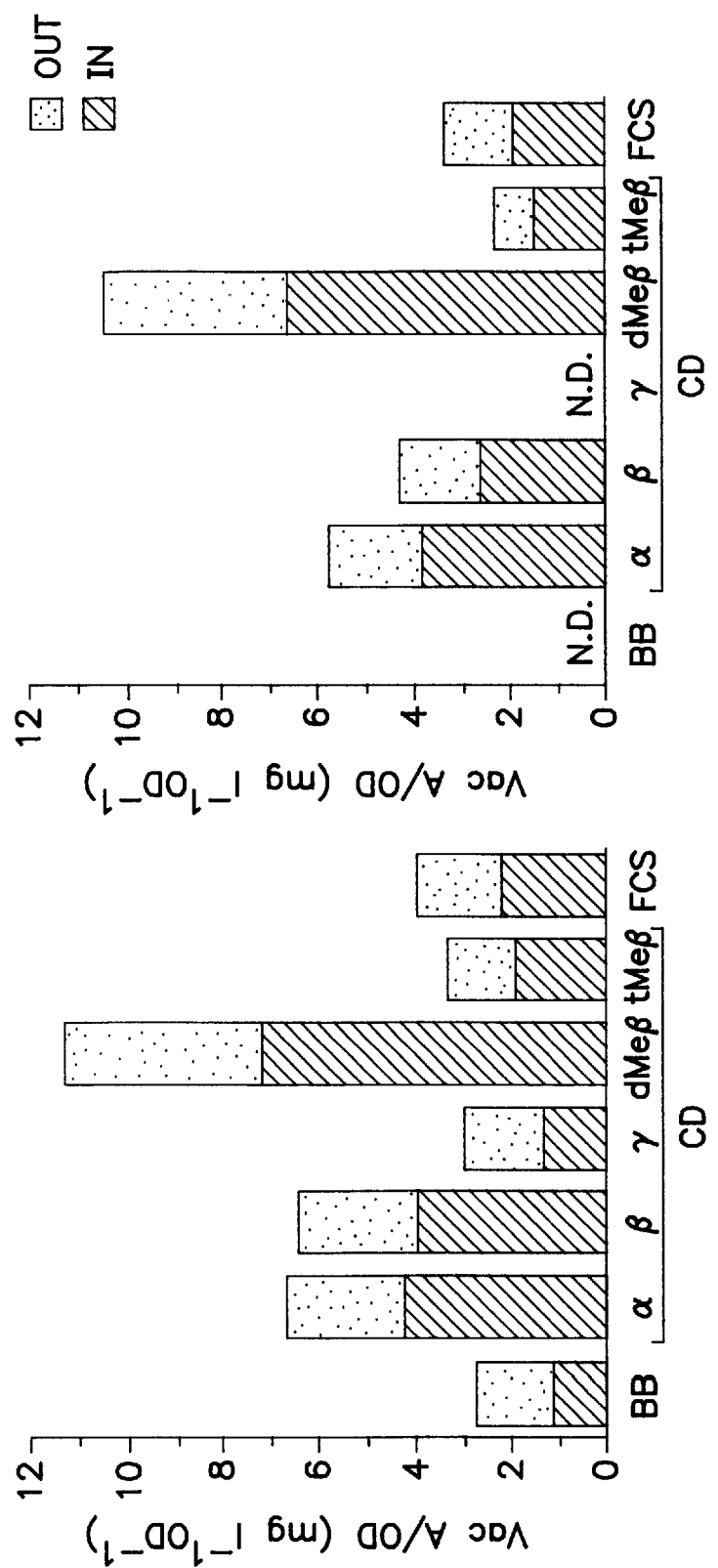

METHOD FOR THE CULTURE OF MICROORGANISMS OF THE GENERA HELICOBACTER, CAMPYLOBACTER AND ARCOBACTER EMPLOYING CULTURE MEDIA COMPRISING CYCLODEXTRINS

This is a continuation-in-part of U.S. application Ser. No. 08/295,081, filed Aug. 24, 1994, pending, which is a continuation of U.S. application Ser. No. 07/962,357, filed Oct. 16, 1992, abandoned.

TECHNICAL FIELD OF THE INVENTION

The present invention relates to a method for the culture of microorganisms of the genera Helicobacter, Campylobacter and Arcobacter, wherein culture media are employed which comprise cyclodextrins.

BACKGROUND OF THE INVENTION

The culture on industrial scale of microorganisms of the genera Helicobacter, Campylobacter and Arcobacter is getting more and more important both for the production of relevant amounts of the same microorganisms and because of the importance of the products which can be produced during the fermentation culture or still for the manufacture of cheap media suitable for the primary isolation of microorganisms belonging to the aforementioned genera. With regard to the importance attained by the above cited microorganisms, it should be considered, for instance, that the *Helicobacter pylori* is recognized as the aetiological agent of type B gastritis, likely the second most disseminated chronic infection in the world after dental caries, and as co-agent of peptic ulcer. Infection with *Helicobacter pylori* has also been associated with increased risk for gastric carcinoma, a disease which may be responsible for one million deaths annually. Forman, et al., *Br. Med. J.*, 302: 1302–1305, 1991. The microbial etiology of these diseases indicates that they might be prevented through vaccination. It is therefore evident that a more developed knowledge of the physiological and pathological properties of said microorganism, knowledge that at present is still very poor due to the difficulty involved in the cultivation, and the large scale cultivation of such microorganism, should be of extreme importance.

The cultures of *H. pylori* are usually carried out by adding to the culture media blood or derivatives thereof (serum, red cells etc.), yolk in concentration ranging between 5% and 20%. Said additives, obviously, cannot be employed on industrial scale because of the drawbacks deriving therefrom for the purification of the culture products, drawbacks which moreover involve high costs for the industry. It is therefore extremely interesting to avail a culture media wherein blood and derivatives thereof are replaced, entirely or partially, by products which do not bring about the above cited disadvantages, without compromising the culture yield though.

SUMMARY OF THE INVENTION

It has been surprisingly discovered, and it makes the object of the present invention, that culture media wherein blood and its derivatives are, at least partially, replaced by cyclodextrins, enable the microorganisms of the genera Helicobacter, Campylobacter and Arcobacter to be cultivated in a similar way and with yield even improved over those obtained with the traditional media.

The present invention therefore relates to a method for the culture of microorganisms of the genera Helicobacter, Campylobacter and Arcobacter with the object of preparing the cell layer of the same microorganisms and/or the specific proteins of pharmaceutical interest produced by the same or still for manufacturing cheap culture media suitable for the primary isolation of microorganisms belonging to the aforementioned genera.

According to a specific embodiment of the present invention said culture method relates to the culture of microorganisms selected from the group consisting of *Camplylobacter jejuni, Campylobacter coli, Campylobacter laridis, Campylobacter jejuni* subspecies *doylei, Campylobacter upsaliensis, Campylobacter hyointestinalis, Campylobacter fetus* subspecies *fetus, Campylobacter fetus* subspecies *venerealis, Campylobacter fennelliae, Campylobacter sputorum* subspecies *bubulus, Campylobacter sputorum* subspecies *fecalis*, and *Campylobacter concisus, Arcobacter nitrofigilis, Arcobacter cryaerophilus*, and *Arcobacter butzleri*. More specifically the invention relates to a method for the culture of *Helicobacter pylori*, and to the production of the about 130 kD (128 kD) protein associated to the cytotoxic activity, the protein exhibiting ureasic activity synthesized by the same microorganism, and the about 90 kD protein associated to vacuolating activity (VacA). The about 130 kD protein is the immunodominant surface exposed antigen of *H. pylori*.

According to a still more specific embodiment of the present invention, blood and/or derivatives thereof are entirely absent from the culture media. The culture is carried out on media, either solid or liquid, comprising cyclodextrins.

In particular cyclodextrins selected from the group consisting of α-cyclodextrin and β-cyclodextrin, optionally methylated, are employed.

According to a specific embodiment of the invention dimethyl-O-β-cyclodextrin is used.

BRIEF DESCRIPTION OF THE DRAWINGS

FIGS. 4a and b depict the VacA production from *Helicobacter pylori* cultured with various cyclodextrins.

DETAILED DESCRIPTION

Figure 1:
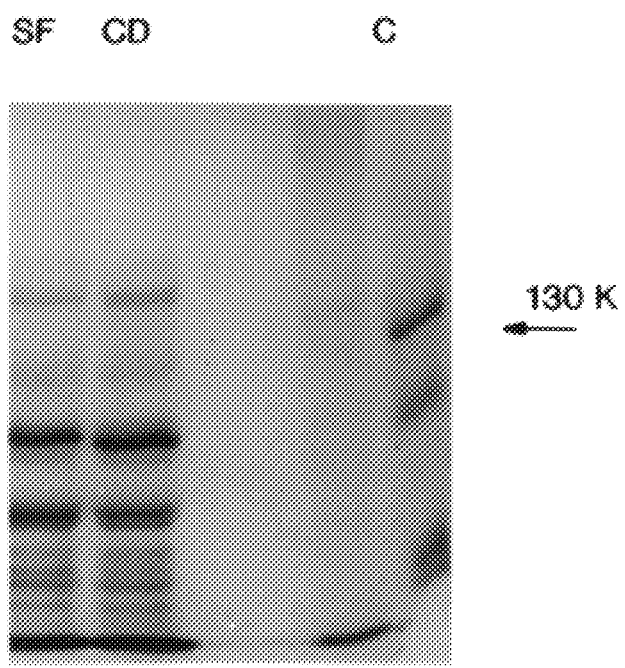
FIG. 1 depicts the amount of about 130 kD protein cytoxicity-associated protein isolated from *Helicobacter pylori* cultures.

As discussed below, *H. pylori* is able to grow for many generations in BB containing several different cyclodextrins (CDs), with the exception of γCD, yielding bacterial growth densities higher than, or comparable to, growth obtained with 1% fetal calf serum, a media supplement traditionally used for *H. pylori* liquid culture.

It is possible that the improved growth of *H. pylori* in media containing cyclodextrins may be due to the capacity of CDs to clathrate certain molecules present in the culture medium. Thus, the CDs may function through complexation of inhibitory factors which are present in the medium, or produced by the metabolism of the microorganism itself, creating a more favorable environment.

The CDs used were composed of 6, 7, or 8 D-glucose units linked 1–4 to form α, β, or γ CD respectively, some being methylated. Each of these cyclic molecules has a hydrophilic shell and a hydrophobic cavity, and can thus form inclusion complexes in which a variety of suitable guest molecules can be accommodated. Differences in culture growth densities permitted by the various CDs tested were observed. These differences may be due to the specific chemical-physical characteristics of each CD, such as the size of the cavity and substitution of the hydroxyl groups. These properties may thus affect the efficiency of complexation of toxic compound(s) in the *H. pylori* medium. Indirect evidence for the existence of inhibitory factors clathrated by CDs is provided by the concentration-dependent effect of dMeβCd. In this case, the plateau of bacterial growth density at dMeβCD concentrations of 2 g $1^{-1}$ and above may indicate a saturable effect on the sequestration of a putative inhibitor.

Recently it has been shown that the growth of *H. pylori* is inhibited by certain polyunsaturated fatty acids (Thompson et al., Gut, 35: 1557–1561, 1994). Additionally, it has been demonstrated that BSA added to the culture medium resulted in the enhanced growth of the bacteria, possibly through the adsorption of unsaturated fatty acids (Hazell and Graham, *J. Clin. Microbiol.*, 28: 1060–1061, 1990). Cyclodextrins may act through a similar mechanism.

The about 130 kD cytotoxicity-associated protein may be extracted from the biomass collected upon centrifugation of the culture media according to the procedure disclosed hereinafter. After washing with phosphate buffer pH 7.4 (PBS) the cell layer is treated with a 6M guanidine HCl in PBS solution at room temperature under stirring. After centrifugation the supernatant is dialysed versus PBS and represents a fraction enriched in 130 kD cytotoxin.

Urease may be purified from the same biomass according to the procedure reported hereinafter. The pellet of bacterial cells is resuspended in 0.25M glycine HCl, pH3, 5 mM EDTA and incubated at 37° C. for 16 hours. The supernatant obtained upon centrifugation at 12,000 rpm, at 5° C. for 30 minutes in a centrifuge Beckman fitted with a JA 20 rotor, is added with two volumes absolute acetone and cooled at –20° C. After keeping for 5 hours at said temperature, the proteic pellet is collected by centrifugation as already described and finally resuspended and dialysed in PBS.

It has now also been found that the method according to the invention can be used for the production of VacA, recently identified as having a key role in the pathology of gastric diseases. (WO 93/18150, incorporated herein by reference.) The production of VacA was quantitatively analyzed in flask cultures grown in the presence of each of the CDs tested, and results indicate that VacA expression was maintained over multiple subcultures in all cases except γCD. Furthermore, a general trend observed is in that the quantity of VacA produced correlated with optical density of the culture achieved.

The culture temperature may vary from 30° to 42° C., and is preferably maintained at 37° C. The culture media is maintained under stirring and in microaerophylic conditions in presence of $CO_2$ and optionally $H_2$.

The method according to the invention has not only simplified, as already said, the culture of the aforementioned microorganisms at issue and the recovery of the proteins produced by them, but it has also allowed the study of the biochemical and physiological (motility) features as well as the chemosensitivity and the pathogenicity of the *H. pylori* to be improved by simplifying it. Given the need for a simplified liquid medium for industrial purposes of *H. pylori* fermentation and antigen recovery, the application of CDs represents a significant improvement over previous supplements commonly employed.

EXAMPLE 1

The strain of *H. pylori* was cultured on Petri dishes containing 20 ml of the agarized culture media Columbia Difco, modified with the addition of 2 g/l dimethyl-O-β-cyclodextrin. The dishes, once inoculated, were incubated in microaerophylic atmosphere at high humidity level (about 95%) at a temperature of 37° C. for 72–96 hours. When the cell layer was clearly apparent on the dishes, the method was prosecuted with the suspension, by means of a wad of sterile cotton wool, of the bacteria in Brucella media until an optical density equivalent to 9 McFarland was achieved. Five millilitres of this suspension were inoculated in a 2000 ml conical flask containing 500 ml Brucella Difco media modified by adding 2 g/l dimethyl-O-β-cyclodextrin, 2.5 mg/l $FeCl_2$, 2.5 mg/l amphotericin B, 10 mg/l trimethoprin, 5 mg/l vancomycin, and 5 U/ml polymixin B. another 5 millilitres were inoculated in a conic flask of the same size as the previous and containing the same medium, where however cyclodextrin is replaced by 10 g/1 fetal serum. The conic flasks were incubated for 72 hours in a rotating incubator at 200 rpm at a temperature of 37° C. in microaerophylic atmosphere having the following composition: $N_2$ 75%, $CO_2$ 10%, $H_2$ 10% and $O_2$ 5%.

After said period the optic density was monitored at 590 nm and a subculture on Columbia agar/blood and a Gram staining were performed in order to verify the purity of the culture. The optic density obtained was equivalent to 2.8 in the conic flask with cyclodextrin and 1.8 in that with fetal serum.

Two samples, 5 g layer each, collected from cultures carried out, as reported above, with either cyclodextrin (CD) or fetal serum (FS) respectively, were treated as follows: after washing with 100 ml PBS, they were centrifuged with a Beckman centrifuge fitted with a JA 20 rotor at 5000 rpm for 30 min at 4° C. The layer was treated with 25 ml 6M guanidine HCl in PBS solution and maintained under agitation for 60 minutes at room temperature. Then the suspensions were centrifuged, as disclosed above, and the supernatants, 20 ml for each sample, were dialysed versus PBS for 16 hours at 40° C. After dialysis a further centrifugation was carried out to remove the insoluble material; the obtained supernatants represent the fractions enriched in the protein of about 130 kD associated to the cytotoxic activity.

As shown in FIG. 1 the amount of the protein of about 130 kD obtained from the two cell layers was comparable, however, with an excess from the culture obtained by using cyclodextrin from which a larger amount of cell layer has been recovered.

EXAMPLE 2

The liquid cultures of *H. pylori* obtained as reported in Example 1 were collected by centrifugation and resuspended in 25 ml, 0.25M glycine HCl, 5 mM EDTA, pH 3 and incubated at 37° C. for 16 hours without agitation.

Figure 2:
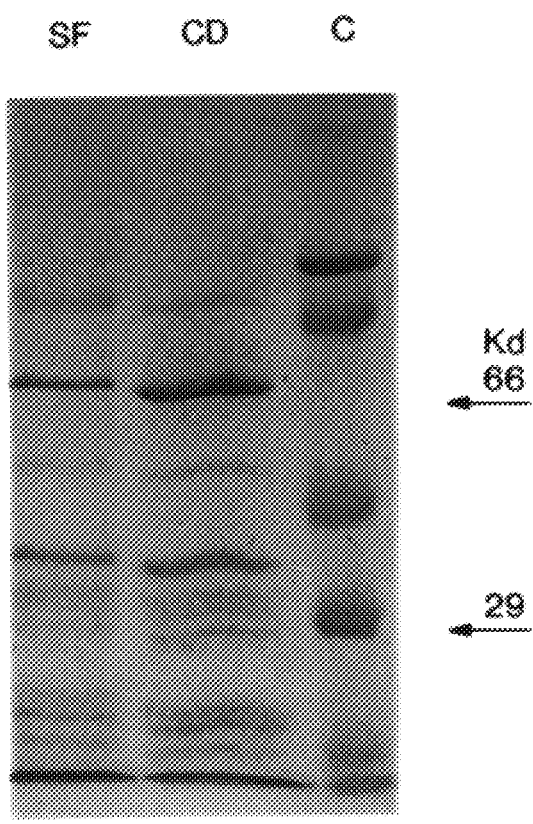
FIG. 2 depicts the amount of urease isolated from *Helicobacter pylori* cultures.

The obtained bacteria suspension was added with 10N NaOH to a pH value of 7.4 and subsequently centrifuged at 12,000 rpm for 30 min at 5° C. The obtained supernatants were quickly cooled in ice/water added with two volumes acetone precooled at –20° C. The suspensions so obtained were maintained at –20° C. for 5 hours and subsequently centrifuged at 12,000 rpm. The recovered pellets were resuspended in 5 ml PBS and dialysed against PBS at 4° C. for 16 hours. Thus obtained samples represent fractions enriched in urease and they are shown in FIG. 2. The comparison of the bands puts in evidence that the bands relative to the two major urease subunits, i.e. 66 and 29 kD, are nearly equivalent in the two samples.

In FIGS. 1 and 2 there are reported the results obtained from the electrophoresis of the cellular layer obtained in Examples 1 and 2 respectively (lane CD in each figure) compared with the cellular layer obtained with the traditional media (lanes SF). Lane C in both figures indicates the standards for the determination of the molecular weight. The electrophoresis was performed in 7% SDS-PAGE on mini-gel according to the method of Laemmli U.K., employing an electrophoretic cell Mini-Protean 2 Biorad® at 200 V for 45 min. The protein bands were stained with Coomassie® R-250.

EXAMPLE 3

Eight strains of *H. pylori*, namely the strain CCUG 17874 and sever further strains isolated from gastric biopsies, were evaluated for their ability to grow on Columbia agar and on Muller-Hinton agar containing either dimethyl-O-β-cyclodextrin (2 g/l) or, in the alternative, 50 g/l defibrinated horse blood. The aforementioned culture media were assayed in their selective form obtained upon addition of one of the two chemotherapeutic mixtures reported hereinafter: Mixture A: 5 mg/l vancomycin, 10 mg/l trimethoprin, 5 mg/l amphotericin B, 5 U/ml polymixin; Mixture B: same as mixture A, but replacing Polymixin by 6 mg/l cefsulodin.

The strains, maintained in Wilkins-Chalgren media with 20% glycerol at −80° C., were thawed, inoculated on dishes of Columbia agar containing 5% defibrinated horse blood, and incubated at 37° C. for 72 hours in microaerophylic conditions. Then the bacterial layer from each strain was suspended in Brucella media up to an optic density of about 6 McFarland. Ten μl of the bacterial suspension were inoculated on each of the aforementioned dishes and smeared with the technique of the isolation. The dishes were incubated as reported above and monitored after 5–7 days.

The colonies which developed on the media containing cyclodextrin, with or without antibiotics, were about 2 mm in size, were in relief, opaque, regularly cut, and with buttery consistence. The features of said colonies did not differ from those of colonies developed on media comprising blood.

The colonies developed on media either with cyclodextrin or with blood showed the same results, peculiar of the species, by the following tests: Gram negative staining; oxidase, catalase and urease positive; nitrate to nitrite reduction; hippurate hydrolysis negative; leucine-aryl-amidase, gamma-glutamyl transpeptidase, acid phosphatase and indoxyl acetate positive.

EXAMPLE 4

Sensitivity assays of *H. pylori* to chemotherapeutics were carried out using Columbia agar comprising dimethyl-O-β-cyclodextrin. The eight strains reported in Example 3 were examined.

The chemotherapeutics tested according to the Kirby-Bauer method were the following: ampicillin (10 μg flat tablet), erythromycin (15 μg flat tablet), clindamycin (2 μg flat tablet), metronidazole (100 μg tablets), and colloidal bismuth subcitrate (De Nol) (100 μg flat tablets). The metronidazole was also tested according to the method designated E-test (AB Biodisk, Solna, Sweden). The tests were carried out either on Columbia agar comprising 0.1–0.2% cyclodextrin or on Columbia agar comprising 5% defibrinated horse blood. Eighty ml of the above cited solid culture media were put in Petri dishes of 150 mm.

The strains were suspended in Brucella media up to an optic density of 4 McFarland and subsequently dispensed on the dishes with a sterile cotton wad. After placement of diskettes and strips, the dishes were maintained for 3–5 days in microaerophylic atmosphere at high level of humidity, at 37° C. After said period of time, the inhibition halos of the different chemotherapeutics and the minimum inhibiting concentrations (MIC) of metronidazole were compared on the dishes containing the media with cyclodextrin and those with defibrinated horse blood. The halos proved to be overlapping.

EXAMPLE 5

Assays of motility on soft agar were performed using the eight strains disclosed in Example 3. The soft agar was prepared by adding, before the sterilization, 5 g DIFCO agar per litre Brucella media. The compared media were those comprising either 0.1–0.2% cyclodextrin or 10% heat inactivated fetal bovine serum.

The inoculation was effected by dipping, about 2 mm, the ring containing the bacterial layer picked up from a dish of agar comprising 0.1–0.2% cyclodextrin. Once inoculated, the dishes were incubated at the same conditions referred to in Example 4 and observed after 5 days. Among the eight tested strains, six showed diffusion within the depth of the agar of both media, which indicates motility, whereas the remaining two did not evidence any diffusion in both media.

EXAMPLE 6

Specimens from 10 patients subjected to diagnostic gastroscopy for dyspepsy were examined. From each patient 5 biopsy specimens were collected from the stomach cavity: one for the histological test; one for the culture on Columbia agar comprising 0.1–0.2% dimethyl-O-β-cyclodextrin, 5 mg/l vancomycin, 10 mg/l trimethoprim, 6 mg/l cefsulodin, 5000U/l polymixin and 5 mg/l amphotericin B; one for the culture on Columbia agar comprising 5% defibrinated blood plus the chemotherapeutic mixture cited above; one for the bacterioscopic examination upon staining of the smears of biopsies on slide with acridine orange; and one for the determination of the urease activity.

The dishes were incubated in microaerophylia at 37° C. and examined after 48 hours and daily during 7 days. The suspected colonies were identified as *H. pylori* by following the procedure disclosed in Example 3.

*H. pylori* was isolated in 5 cases: in three cases on both media, in a fourth case on cyclodextrin medium only, and in a fifth case on blood medium only. The *H. Pylori* colonies on Columbia agar with cyclodextrin were already well visible after 48 hours; by the fifth day the colony sizes were similar to those developed on Columbia agar comprising blood. The selectivity of the two media in relation to the bacteria accompanying *H. pylori* in the same specimen from the biopsy proved to be identical. This experimentation confirms the suitability of cyclodextrin comprising media for the primary isolation of *H. pylori* from gastric biopsies.

EXAMPLE 7

*Helicobacter Pylori* CCUG 17874 (type strain, Culture Collection of the University of G oteborg, Sweden) was used in this and the following examples to determine the effect of CDs over many bacterial generations, we performed five sequential subcultures.

Columbia blood agar (CBA) (Difco, Detroit, Mich., USA), supplemented with the following antibiotics (Sigma, St. Louis, Mo., USA) cefsulodin 6 mg/l, vancomycin 5 mg/l, trimethoprim 10 mg/l, amphotericin B 8 mg/l, was used as solid medium. Brucella broth (BB) (Difco) supplemented with cyclodextrins (Cyclolab, Pusztaszeri U., H 1025 Budapest, Hungary) at the indicated concentrations, or 1% fetal calf serum (FCS) (GIBCO Laboratories, Grand Island, N. Y., USA) and the antibiotics mentioned above, was used as liquid medium. The cyclodextrins used were: α cyclodextrin (αCD), β cyclodextrin (βCD), γ cyclodextrin (γCD), (2, 6-di-o-methyl)-β-cyclodextrin (dMeβCD) and (2, 3, 6-tri-o-methyl)-0-cyclodextrin (tMeβCD).

Frozen aliquots for inocula were prepared from flask cultures of $2 \times 10^8$ CFU/ml diluted 1:2 with a solution composed of 40% glycerol, 20% fetal calf serum and 0.4% dMeβCD. The suspension obtained was distributed in 1.5 ml vials and frozen at $-80°$ C.

One aliquot of frozen bacterial suspension was spread on agar plates (CBA) and incubated at 36° C. for 72 hours. The plates were placed inside anaerobic jars and BBL Campy Pak envelopes (Becton Dickinson, Le Pont de Claix, France) were used to generate the proper microoxic conditions. Liquid cultures were performed in 130 ml Erlenmeyer flasks containing 30 ml of liquid medium. Bacteria were harvested from plates and resuspended in BB. This solution was used to inoculate flasks at an initial $OD_{590}=0.1$. The flasks were incubated at 36° C. with shaking (100 rpm, 2.5 cm throw) in microaerobic conditions as above. Subcultures were performed by diluting aliquots of the 48 hour culture into fresh medium to an initial $OD_{590}=0.1$.

Growth was monitored by optical density at 590 nm (Perkin Elmer 35 spectrophotometer). Purity checks of the samples were made by Gram staining and by subculturing samples on CBA plates which were incubated in a normal atmosphere at 37° C. for 24 hours.

Each subculture was grown for 72 hours in the presence of various CDs at a concentration of 2 grams/liter$^{-1}$. Control subcultures were performed using Brucella broth containing 1% fetal calf serum, according to previously published methods (Morgan et al., *J. Clin. Microbiol.*, 25: 2123–2123, 1987, incorporated herein by reference), or Brucella broth alone. At various time points, samples were collected and bacterial growth was measured as the optical density at 590 nm.

Figure 3B:
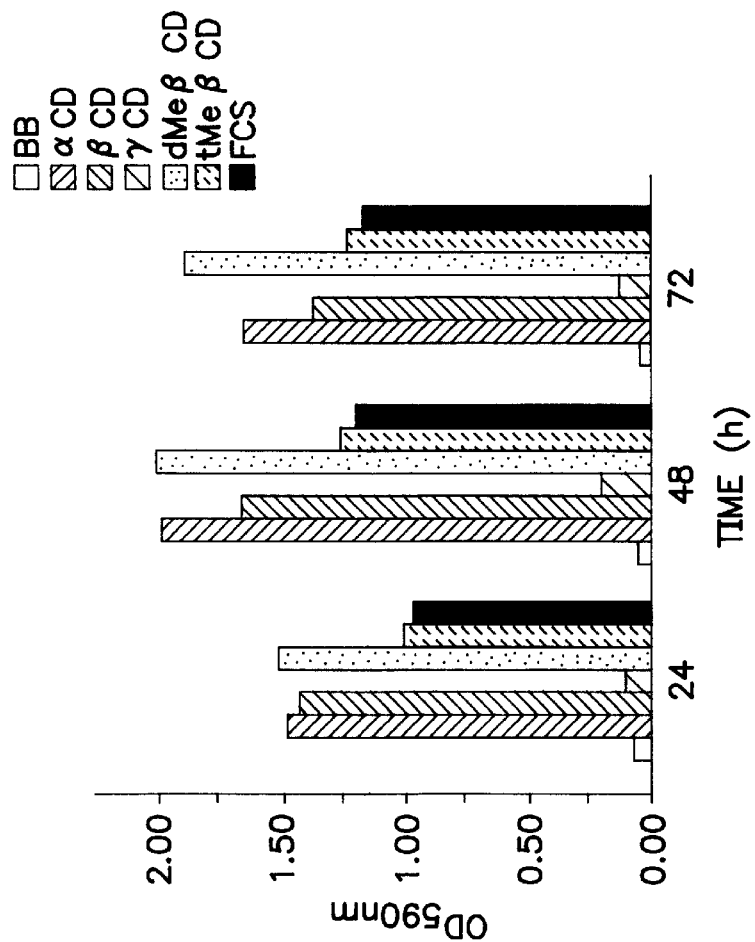
FIGS. 3a and b depict the growth densities of *Helicobacter pylori* cultured with various cyclodextrins in liquid medium.
Figure 3A:
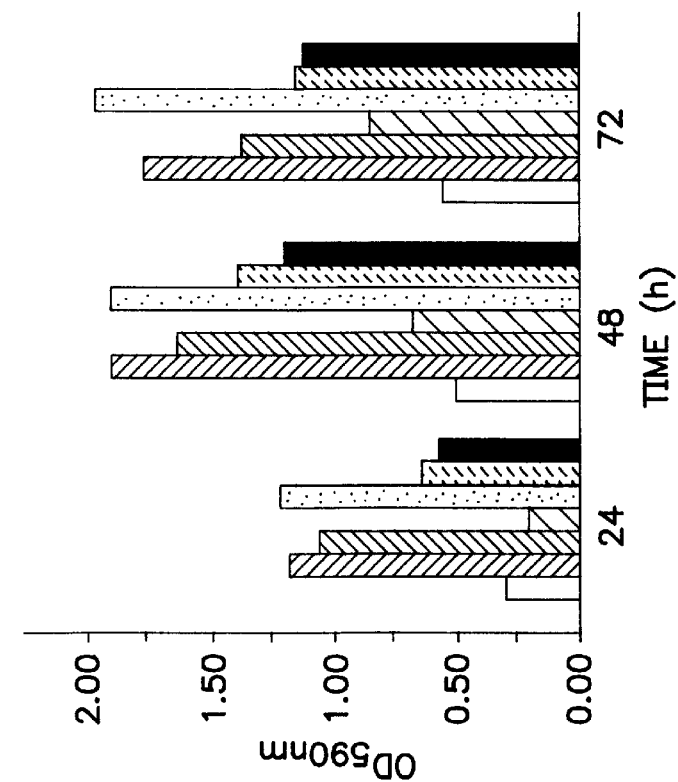

The growth data of the bacteria at 24, 48, and 72 hours in the initial and fifth subcultures are presented in FIGS. 3a and b, respectively. Data analysis reveals that αCD and dMeβCD yielded growth at approximately 2 OD units in each subculture. βCD and tMeβCD also permitted robust growth, resulting in slightly lower culture densities than aCD or dMeβCD. Brucella broth supplemented with 1% FCS yielded growth to approximately 1.2 OD, a level comparable to that obtained with βCD or tMeβCD. βCD or BB alone did not sustain a significant growth after five subcultures.

EXAMPLE 8

For the purpose of production of industrial quantities of antigen for vaccine research, the use of CDs in growth medium should preferably result in consistent expression of VacA over the course of several generations. Therefore, VacA production was analyzed in parallel with culture density from both the initial and fifth subcultures.

After 48 hours, culture samples were normalized to an $OD_{590}$ of 1 and were centrifuged at 8300×g for 10 minutes. The pellets were separated from supernatants and both were frozen at −20° C. Pellet fractions were resuspended appropriately to yield an $OD_{590}$=1 in SDS-PAGE loading buffer containing 3β mercaptoethanol. Both fractions were analyzed by 9% SDS-PAGE using a BioRad Mini Prot II apparatus according to Laemmli. Proteins were transferred to nitrocellulose filters (Schleicher & Schuell, Dassel, Germany) and incubated overnight with polyclonal antisera raised against the VacA protein (Telford et al., *J. Exp. Med.*, 179:1653–1658, 1994). Immunoreactive bands were visualized after incubation with a horseradish-peroxidase conjugated secondary antibody (Sigma), followed by a 4-chloronapthol staining. For each immunoblot, the amount of cytotoxin in culture supernatant was estimated using a calibration curve obtained with known quantities of purified VacA protein. Quantitative estimation was made by ultrascanner densitometry using an Image Master Desk Top Scanner (Pharmacia LKB, Uppsala, Sweden) in 1D reflectance mode.

The results are depicted in FIGS. 4*a* and *b*. The results from the first (4*a*) and fifth (4*b*) subculture are shown. "N.D." represents not detectable. The fraction of VacA present in the supernatant (out) and VacA associated with bacterial cells (in) was calculated using a standard curve. With the exception of γcyclodextrin, VacA production was comparable to the fetal calf serum-containing medium with the CDs tested. The addition of dMeβCD to growth medium resulted in a significantly higher yield of VacA as compared to the other CDs, or medium supplemented with 1% fetal calf serum.

EXAMPLE 9

From our previous analysis, dMeβCD was chosen for a detailed study utilizing CD concentrations from 0.25 g $1^{-1}$ to 6 g $1^{-1}$. Culture conditions were as in the previous examples. After 48 hours of growth, optical density was measured and bacteria were harvested and separated into supernatant and pellet fractions. These fractions were analyzed by quantitative Western blot, and the results are summarized in Table 1.

TABLE 1

| dMeβCD ($gl^{-1}$) | $OD_{590nm}$ | $VacA_{pellet}$/OD ($mgl^{-1}$ $OD^{-1}$) | $VacA_{supernatant}$/OD ($mgl^{-1}$ $OD^{-1}$) | VacA total production ($mgl^{-1}$) |
|---|---|---|---|---|
| 0.25 | 1.10 | 1.80 | 2.60 | 4.80 |
| 0.50 | 1.30 | 1.90 | 2.80 | 6.10 |
| 1.00 | 1.56 | 3.60 | 3.80 | 11.50 |
| 2.00 | 1.85 | 6.50 | 4.00 | 19.50 |
| 4.00 | 1.90 | 7.80 | 4.20 | 22.80 |
| 6.00 | 1.80 | 8.10 | 4.00 | 21.80 |

VacA production was measured as total immunoreactive material recovered. VacA protein associated with supernatant and pellet fractions was normalized for culture optical density, in order to analyze growth-independent effects of dMeβCD. Both the optical density of *H. pylori* cultures and VacA production increased in a linear fashion with dMeβCD concentration reaching a plateau at 2 g $^{-1}$.

The foregoing examples are meant to illustrate the invention and not to limit it in any way. Those skilled in the art will recognize that changes can be made which are within the spirit and scope of the invention as set forth in the appended claims.

What is claimed is:

1. A method for preparing the about 130 kD surface exposed, immunodominant cytotoxicity-associated protein of *Helicobacter pylori* comprising:

a) culturing *Helicobacter pylori* in a culture medium useful for cultivating *Helicobacter pylori* containing blood products and/or derivatives thereof wherein the blood products and/or derivatives thereof are replaced with a cyclodextrin of seven glucose units or less; and b) isolating said protein from the culture.

2. The method according to claim 1 wherein the cyclodextrin is 2,6-di-O-methyl-β-cyclodextrin.

3. The method according to claim 2 wherein the concentration of 2,6-di-O-methyl-β-cyclodextrin is from about 0.25 grams/liter to about 6 grams/liter.

4. A method for preparing the about 130 kD surface exposed, immunodominant cytotoxicity-associated protein of *Helicobacter pylori* comprising:

a) culturing *Helicobacter pylori* in a culture medium useful for cultivating *Helicobacter pylori* containing blood products and/or derivatives thereof wherein the blood products and/or derivatives thereof are replaced with a cyclodextrin other than unsubstituted γ-cyclodextrin; and b) isolating said protein from the culture.

5. The method according to claim 4 wherein the cyclodextrin is 2,6-dimethyl-O-β-cyclodextrin.

6. The method according to claim 5 wherein the concentration of 2,6-di-O-methyl-β-cyclodextrin is from about 0.25 grams/liter to about 6 grams/liter.

* * * * *